US006837892B2

(12) United States Patent
Shoham

(10) Patent No.: US 6,837,892 B2
(45) Date of Patent: Jan. 4, 2005

(54) MINIATURE BONE-MOUNTED SURGICAL ROBOT

(75) Inventor: Moshe Shoham, Hamovil (IL)

(73) Assignee: Mazor Surgical Technologies Ltd., Nesher (IL)

(*) Notice: Subject to any disclaimer, the term of this patent is extended or adjusted under 35 U.S.C. 154(b) by 39 days.

(21) Appl. No.: 09/912,687

(22) Filed: Jul. 24, 2001

(65) Prior Publication Data

US 2002/0038118 A1 Mar. 28, 2002

Related U.S. Application Data

(60) Provisional application No. 60/220,155, filed on Jul. 24, 2000.

(51) Int. Cl.[7] .................................................. A61B 19/00
(52) U.S. Cl. ........................................ 606/130; 74/490.01
(58) Field of Search ................................. 606/1, 53, 79, 606/80, 86, 60, 62, 63, 130; 623/24, 25; 74/490.01, 490.05

(56) References Cited

U.S. PATENT DOCUMENTS

| 4,457,311 | A | * | 7/1984 | Sorenson et al. ........... 600/447 |
| 5,167,165 | A | | 12/1992 | Brucher et al. |
| 5,236,432 | A | * | 8/1993 | Matsen et al. ................ 606/88 |
| 5,408,409 | A | * | 4/1995 | Glassman et al. .......... 600/407 |
| 5,410,638 | A | | 4/1995 | Colgate et al. |
| 5,546,942 | A | * | 8/1996 | Zhang ......................... 600/427 |
| 5,674,221 | A | * | 10/1997 | Hein et al. ..................... 606/54 |
| 5,791,231 | A | * | 8/1998 | Cohn et al. ..................... 92/88 |
| 5,806,518 | A | * | 9/1998 | Mittelstadt ................... 600/407 |
| 5,814,038 | A | * | 9/1998 | Jensen et al. ................... 606/1 |
| 5,824,085 | A | * | 10/1998 | Sahay et al. ................ 128/898 |
| 6,226,548 | B1 | * | 5/2001 | Foley et al. ................ 600/426 |
| 6,231,526 | B1 | * | 5/2001 | Taylor et al. ............... 600/587 |
| 6,236,875 | B1 | * | 5/2001 | Bucholz et al. ............. 600/407 |
| 6,246,200 | B1 | * | 6/2001 | Blumenkranz et al. ...... 318/568.11 |
| 6,322,567 | B1 | * | 11/2001 | Mittelstadt et al. .......... 606/130 |

FOREIGN PATENT DOCUMENTS

| EP | 0 654 244 A1 | 5/1995 |
| WO | WO 91/07726 | 11/1990 |

OTHER PUBLICATIONS

Besl, Paul J., *A Method for Registration of 3–D Shapes*, IEEE Transactions on Pattern Analysis and Machine Intelligence, vol. 14, No. 2, p. 239–256 (1992).

Brack, C. et al., *Accurate X–Ray–based Navigation in Computer–Assisted Orthopedic Surgery*, Computer Aided Radiology and Surgery, Elsevier Science B.V., p. 716–722 (1998).

Hamadeh, Ali et al., *Automated 3–Dimensional Computed Tomographic and Fluoroscopic Image Registration*, Computer Aided Surgery 3:11–19 (1998).

(List continued on next page.)

*Primary Examiner*—Julian W. Woo
*Assistant Examiner*—Victor Nguyen
(74) *Attorney, Agent, or Firm*—Morgan Lewis & Bockius LLP

(57) ABSTRACT

A miniature surgical robot and a method for using it are disclosed. The miniature surgical robot attaches directly with the bone of a patient. Two-dimensional X-ray images of the robot on the bone are registered with three-dimensional images of the bone. This locates the robot precisely on the bone of the patient. The robot is then directed to pre-operative determined positions based on a pre-operative plan by the surgeon. The robot then moves to the requested surgical site and aligns a sleeve through which the surgeon can insert a surgical tool.

29 Claims, 5 Drawing Sheets

OTHER PUBLICATIONS

Hamadeh, Ali et al., *Towards automatic registration between CT and X-ray images: cooperation between 3D/2D registration and 2D edge detection*, Medical Robotics and Computer Assisted Surgery, p. 39–46 (1995).

Hofstetter, R., et al., *Fluoroscopy Based Surgical Navigation—Concept and Clinical Applications*, Computer Aided Radiology and Surgery, Elsevier Scient B.V., p. 956–960 (1997).

Lemieux, L. et al., *A patient-to-computed-tomography image registration method based on digitally reconstructed radiographs*, Medical Physics, vol. 21, No. 11, p. 1749–1760 (1994).

Lorensen, William E. et al., *Marching Cubes: A High Resolution 3D Surface Construction Algorithm*, ACM Computer Graphics, vol. 21, No. 4, p. 163–168 (1987).

Murphy, Martin J., *An automatic six-degree-of-freedom image registration algorithm for image-guided frameless stereotaxic radiosurgery*, Med. Phys.. 24 (6), p. 857–866 (1997).

Sima'an, N. et al., *Design Considerations of New Six Degrees-of-Freedom Parallel Robots*, Proceedings of the IEEE International Conference on Robotics & Automation, p. 1327–1333 (1998).

Tang, Thomas S.Y., *Calibration and Point-Based Registration of Fluoroscopic Images*, Thesis submitted to Dept. of Computing and Information Science, Queen's University, Kingston, Ontario, Canada (1999).

Tsai, Roger Y., *A Versatile Camera Calibration Technique for High-Accuracy 3D Machine Vision Metrology Using Off-the-shelf TV Cameras and Lenses*, IEEE Journal of Robotics and Automation, vol. RA–3, No. 4, p. 324–344 (1987).

Yaniv, Z. et al., *Fluoroscopic Image Processing for Computer-Aided Orthopaedic Surgery*, Computer Science 1496, Elsevier et al. eds., p. 325–334 (1998).

* cited by examiner

MINIATURE BONE-MOUNTED SURGICAL ROBOT

This application claims priority to U.S. Provisional Application Ser. No. 60/220,155, filed Jul. 24, 2000.

TECHNICAL FIELD

The present invention relates to a robotic device. Particularly, this invention relates to a robotic device that attaches to a bone of the patient and aids or performs surgical procedures.

BACKGROUND OF THE INVENTION

Generally, robots are used in many different industries for many different applications. One industry, for example, is the medical industry that uses robots in applications including assisting the surgeon during surgical procedures. Robots are especially suited for some surgical tasks because they can be constructed to be very steady, computer controlled, and precise in their movements. Characteristics such as these can be especially helpful during surgery on sensitive areas, such as, for example, the vertebral column but are applicable throughout the body.

Typical vertebral column surgical procedures include vertebral fusion, insertion of medical devices such as pedicle screws, discography, percutaneous discectomy, or the like. These procedures typically require a large invasive operation that exposes the patient to a high risk of infection, excessive trauma, fluid loss, post operative pain, scaring, and a lengthy recovery time. Some difficulties relating to surgery on the vertebral column include micro-movement of the vertebral column during the operation, inherently small target objects of the procedure such as the pedicles, extremely delicate nearby nerve tissue, and limited operating room space because large equipment is needed to aid in the procedure, such as C-arm X-ray devices. Furthermore, the patient and operating room staff are exposed to large doses of radiation because these procedures require repeated X-raying and/or fluoroscoping of the surgical site so the surgeon can view the position of surgical tools or implants relative to non-visible body parts.

A need exists for a device that can assist minimally invasive surgery with low radiation exposure while allowing the surgeon to precisely align and control or monitor the surgical procedure. Some prior art devices have attempted to accomplish this however, these devices are either too complicated, not sufficiently accurate, or consume too much operating room space.

One such device is disclosed in U.S. Pat. No. 6,226,548. This device combines a navigation system, a bone mounted apparatus, and surgical tools that communicate with the navigation system. This apparatus primarily consists of a clamp that attaches to the patient's spine and extends outward forming a reference arc bearing emitters or a tracking means. All the surgical tools used in this procedure are fined with emitters or a tracking means similar to the reference arc. The surgical suite is fitted with a navigation system capable of recognizing the emitters or tracking means of the reference arc and surgical tools, a computer system for interpreting the location of the tools, and a video display for the surgeon. After surgically placing the clamp and reference arc on the patient a CT or MRI is taken creating a three-dimensional image of the patient with the attached device. When the patient is in place in the surgical suite with the attached reference arc the navigation system locates the arc and the surgical tools and displays them, relative to each other, on the three-dimensional CT scan.

While the device disclosed in the '548 patent offers some advantages in terms of accuracy and reduced trauma, the advantages of this type of prior art device are limited. The critical part of a surgical tool that must be monitored is the working end of the tool, whether that be a screwdriver or a drill bit or the like. These cannot be tracked with such prior art systems. Transmitters or emitters cannot be attached to the working ends of tools so the computer must estimate the location of the working end by locating the tool generally and extrapolating. This causes inaccuracy and errors that cannot be tolerated in spinal surgery or other high accuracy procedures where the smallest error can result in a serious and permanent outcome. Also, prior art devices such as these are hand held by the surgeon and thus, limited in accuracy to the surgeon's ability to hold and align the tool.

Furthermore, when using this system, the user must be cautious to not block the line-or-sight between the tool mounted emitters or receivers, the reference arc bearing emitters or receivers, and the navigation system. This can severely limit the ability of the surgeon or surgical team as the tool may actually limit their ability to aid the patient. Also, while such prior art systems do reduce the incision size, they complicate the surgical procedure. Usually a patient is brought into a surgical suite ready for a procedure, the procedure is performed, completed, and the patient leaves. However, the '548 patent system requires the patient to be put through a surgical procedure to affix the clamp and referencing arc, then the patient is transported to a CT or MRI, then transported back to the surgical suite in a non-sterile condition for the substantial portion of the procedure to commence. Finally, this system has many components, such as the navigation system and the computer output unit, that clutter up the already limited space in the surgical suite.

Therefore, there is a need in the art for a device with high precision and accuracy that can assist the surgeon in aligning the working end of the surgical tool such that delicate procedures can be preformed percutaneously with minimal radiation exposure to both the patient and the surgical staff.

SUMMARY OF THE INVENTION

The present invention is directed to a device and method for assisting in surgical procedures. According to the invention, a robot is disclosed that precisely positions a surgical tool with respect to a surgical site. The robot attaches to the bone of a patient with a clamp or with wires such as K-wires. Actuators extend from the robot base and move away from and toward the base member. This manipulates balls that rotate within spherical swivel joints that in turn align a sleeve. A surgical tool such as a screw driver or a drill bit is inserted through the sleeve and thus is precisely aligned with a site requiring surgery.

The present invention also includes a method for using the robot to assist in surgical procedures. Initially, three dimensional images are taken of the patient and the surgeon performs pre-operative planning of the procedure to be done on the images. This creates parameters that will later be used to direct the robot to the location where the surgical procedure is required. The robot is then attached to the patient by the clamp or the k-wire. C-arm images are taken of the patient with the attached clamp and these images are co-registered and calibrated such that a precise image of the bone with the robot attached is generated. This image is then registered, or matched, with the three dimensional image. This is accomplished in a highly efficient and accurate manner by taking small windows of the images where the surgery is to take place and registering these small portions.

The small windows are chosen off the images by locating the bone attached clamp and selecting a window according to pre-operative calculation of the bone-robot attachment location. After these windows are chosen and registered, the remaining bone is registered by aligning the registered windows. At this point the robot is located precisely on the bone of the patient in the three dimensional image and can be manipulated by the surgeon to a pre-operative planned location for percutaneous insertion of surgical tools, medical devices, or implants.

BRIEF DESCRIPTION OF THE DRAWINGS

For a better understanding of the nature, objects, and function of the present invention, reference should be made to the following detailed description in conjunction with the accompanying drawings, in which.

Like reference numerals refer to corresponding elements throughout the several drawings.

DETAILED DESCRIPTION OF THE PREFERRED EMBODIMENT

Figure 1:
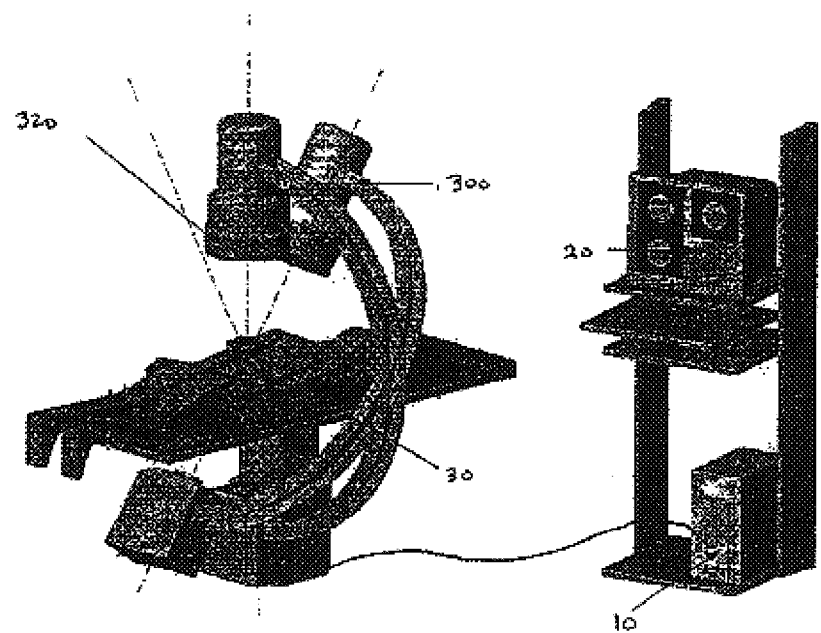
FIG. 1 is an overview of an embodiment of a surgical system showing a control unit with a display, C-arm with a calibration phantom attached, and a robot used for aligning surgical tools attached to the patient according to the present invention.

Referring to the illustrations and particularly to FIG. 1 it can be seen that a preferred embodiment of the present invention generally includes an image guided, robot assisted, surgical system. Included in this system generally, as shown in FIG. 1, is a bone attached surgical robot 30; a control unit 10 that matches data from CT scans and C-arm images to locate robot 30 on the patient's bone and allows a surgeon to control robot 30, through the use of a mouse, joystick, touch screen, or the like; and video display 20. Control unit 10 generally includes a CPU and user interface communicating with display 20 and robot 30.

Figure 2:
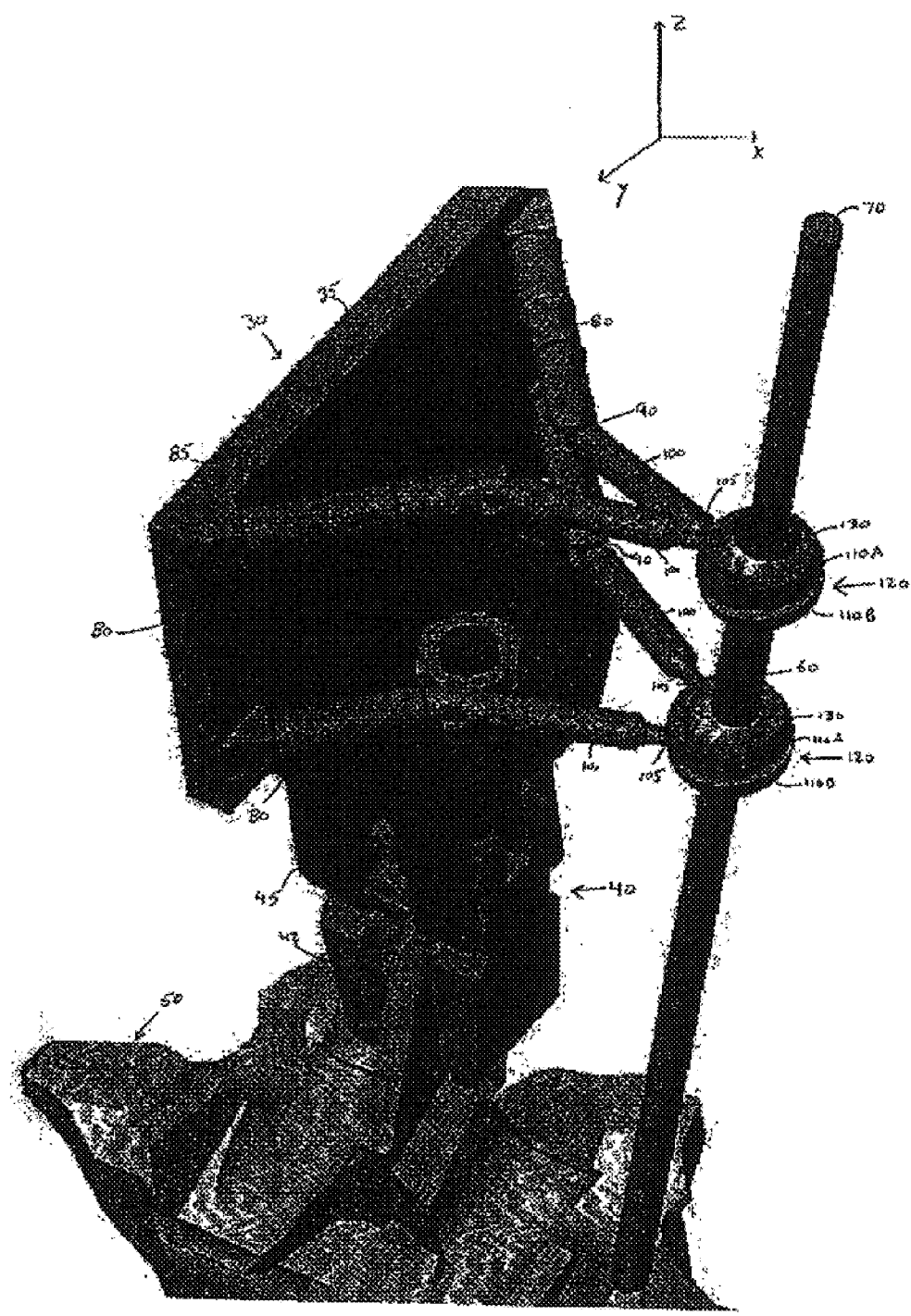
FIG. 2 is a perspective view showing a miniature surgical robot attached to a bone and aligning a surgical tool in an embodiment of the invention.

FIG. 2 illustrates robot 30 according to one embodiment of the present invention attached with clamp 40 to vertebra 50. Robot 30 aligns sleeve 60 through which surgical tool 70 such as a screwdriver, drill bit, Kirschner wire (K-wire), or the like can be inserted and precisely aligned with a site requiring a surgical procedure and thus, the operation can be conducted percutaneously or in traditional open procedures.

In a preferred embodiment of the invention, robot 30 includes base 35 that sits vertically on clamp adaptor 45. At least two pair of actuators 80 extend from base 35. The actuators 80 extend from the base 35 forming a fixed angle 85 between base 35 and actuator 80. This angle is generally between about 15–90 degrees and more preferably about 45 degrees. In one preferred embodiment, the points of attachment of actuators 80 are spaced apart by about 50 mm in the Z direction and about 50 mm in the Y direction. Each actuator 80 is capable of operating independently from the other actuators 80. Actuator 80 is similar to known linear actuators and includes a housing, a motor, a lead screw, an electrical connection, and a position sensor such as an optical encoder, an LVDT, or the like. In a preferred embodiment each actuator is approximately 5 mm in diameter and approximately 35 mm in length.

The end of actuator 80 that is not fixedly attached to base 35 contains hinge joint 90. Hinge joint 90 links actuator 80 to rigid member 100. In a preferred embodiment member 100 is about 4 mm in diameter and 40 mm in length. Hinge joint 90 permits member 100 to freely rotate through about 270 degrees on an axis that runs parallel to base 35. The other end of the rigid member 100 is fixed with solid connection 105 to ring member 110. There is no movement between rigid member 100 and ring member 110 at solid connection 105.

Upper ring member 110A and lower ring member 110B, solidly connected to individual rigid members 100, come together at spherical swivel joint 120. Each ring member 110 forms one half of an outer race of spherical swivel joint 120. Ring members 110 are free to rotate with respect to one another, but are held fixedly from separating in the Z axis direction. Contained between upper ring member 110A and lower ring member 110B, and free to swivel, is ball 130. Passing through ball 130 is sleeve 60. Sleeve 60 passes through both upper and lower balls 130, forming an aligning axis through which surgical tool 70 is passed. As actuators 80 extend and retract, hinge joints 90 freely rotate about the Z axis and balls 130 swivel in the spherical swivel joints 120 formed by upper and lower ring members 110. A hollow axis is formed by the sleeve passing through each of upper and lower balls 130 such that a surgical tool 70 can be inserted through and be accurately aligned with the working location.

According to the present invention the above described robot 30 is just one example of a robot configured for surgical assistance that may be utilized with the system according to the present invention. Other robot configurations that could satisfy the same tasks include, for example, parallel robots constructed to the required dimensions. Such robots may be defined by their joint types, e.g. a universal spherical revolute (USR) robot, a revolute spherical prismatic (RSP) robot, or a double circular triangular (DCT) robot.

The USR robot has three identical kinematic chains, each with two links, connecting the base and the moving platform. The connection at the base platform is by a universal joint and the moving platform is connected by a revolute joint, then these two links are connected by a spherical joint.

The RSPR robot has three identical kinematic chains each with two links connecting the base and the moving platform. The lower link is connected through a revolute joint, the upper link, a prismatic actuator is attached tho the lower link with a spherical joint and to the moving platform with a revolute joint.

Figure 3:
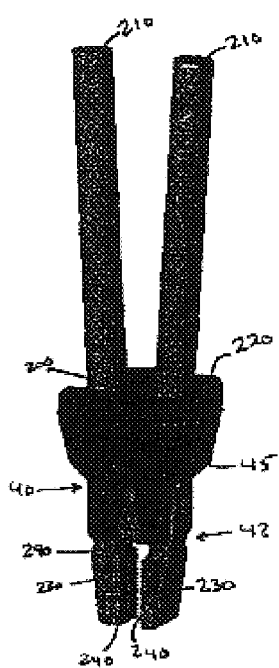
FIG. 3 is a perspective view showing a clamp for attaching to a bone and adaptor for receiving a robot in an embodiment of the invention.
Figure 4:
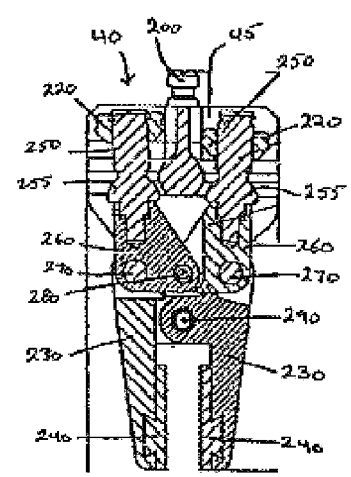
FIG. 4 is a cross-sectional view of FIG. 3.

The DCT robot is a new structure composed of planar mechanisms, each with 3 degrees of freedom. These two planar mechanisms comprise a stationary circle and a moving triangle to theoretically provide higher orientation capacity. Further details are described in Simaan, et al., "Design Considerations of new types of Six-Degrees-of- Freedom Parallel Manipulators," *IEEE International Conference on Robotics and Automation*, Belgium, 1998, which is incorporated by reference herein. In general there are numerous structures of parallel robots. One skilled in the art will appreciate that any robot with multiple degrees of freedom may be utilized for surgical assistance In a preferred embodiment of the invention, robot 30 is attached with the bone of a patient by clamp 40. As shown in FIGS. 3 and 4, clamp 40 comprises bone clamping portion 42 and clamp adaptor 45. Initially, handles 210 extend from clamp 40 and allow a user to hold, align, and affix clamp 40 onto a bone of the patient. The base of the handles 210 fit over nuts 220, shown in FIG. 4, located on clamp 40. When clamp 40 is in place, the user pushes handles 210 toward each other to close jaws 230 onto the selected bone. When handles 210 are fully closed, or pushed together, a first locking (described below) occurs and clamp 40 is locked in place on the bone. The user then rotates handles 210 in a clockwise direction, turning and tightening nuts 220. Nuts 220 tighten down on threaded studs 250 and pinch clamp adaptor 45 onto bone clamping portion 42. This causes a second locking of clamp 40 into place on the bone. The base of each threaded stud 250 has a spherical mating surface 255 so that when clamp adaptor 45 is tightened down onto bone clamping portion 42 the clamp adaptor can self align itself on spherical mating surface 255 of stud 250. This allows the top surface of clamp adaptor 45 to maintain a horizontal surface for receiving the robot base 35. The handles, 210, are then removed by pulling straight up and away from the clamp 40. Protruding from the top surface of clamp adaptor 45 are connection pins 200. Connection pins 200 align with receiving holes in robot base 35 and when inserted lock robot 30 into place by some type of a snap ring or spring and ball bearing or plunger ball/pin.

With reference specifically to FIG. 4, it can be seen that threaded studs 250 are embedded in levers 260. Left and right levers 260 are connected together by upper center hinge 280. The other end of levers 260 connect with respective jaws 230 through side axis hinge 270. Left and right jaws 230 are connected together by main pivot 290 around which the jaws rotate. When a user pushes handles 210 together to close jaws 230, upper center hinge 280 is pushed downward and at the same time side axis hinges 270 rotate around the main pivot 290. The first locking occurs when upper center hinge 280 is pushed below the center line formed between left and right side axis hinges 270, and clamp 40 locks onto the bone. When clamp 40 is in the fully closed and locked position, jaws 230 are parallel to each other and separated by a set distance. The set closing distance between jaws 230 can be altered for different bone attachment applications by exchanging re-moveable jaw inserts 240 with the same of a different thickness.

Figure 7:
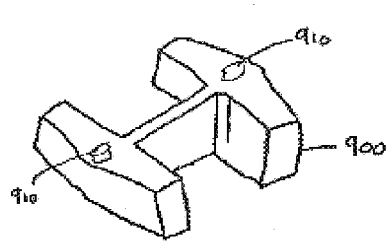
FIG. 7 is a perspective view of a spacer used to extend the clamp.

FIG. 7 illustrates spacer 900 that can be attached to the top surface of clamp adaptor 45 to ensure that robot 30 remains above the working area and out of any tissue that might occur when a patient has unusual body proportions. Spacer 900 attaches to connector pins 200 of clamp adaptor 45 and provides connector pins 910, similar to connector pins 200, for robot 30 attachment to the top surface of the spacer 900.

Figure 8:
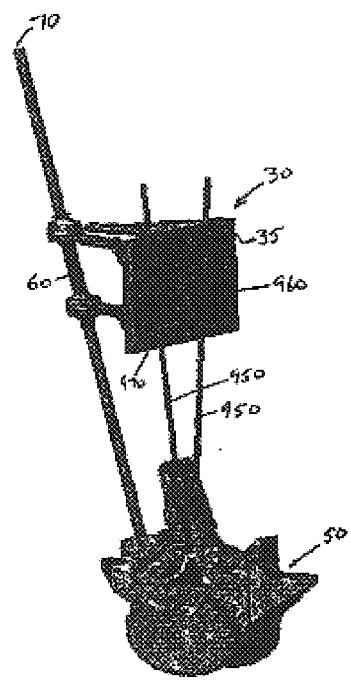
FIG. 8 is a perspective view showing a miniature surgical robot for aligning a surgical tool attached to a bone by K-wires in an embodiment of the invention.

Above described clamp 40 is an example of one embodiment according to the invention by which a robot may be attached to a bone for assisting in a surgical procedure. Other attachment devices can also be incorporated with a robot such as, for example, K-wire connections. FIG. 8 illustrates such a K-wire connection. K-wires 950 are inserted into the bone by standard surgical procedures. Robot base 35 contains an elongated slot through which K-wires 950 are inserted. Screw 960 can then be turned and tighten pinch plate 970 against robot base 35 pinching K-wires 950 between pinch plate 970 and robot base 35 holding robot 30 tight with respect to K-wires 950 and bone 50.

Figure 5:
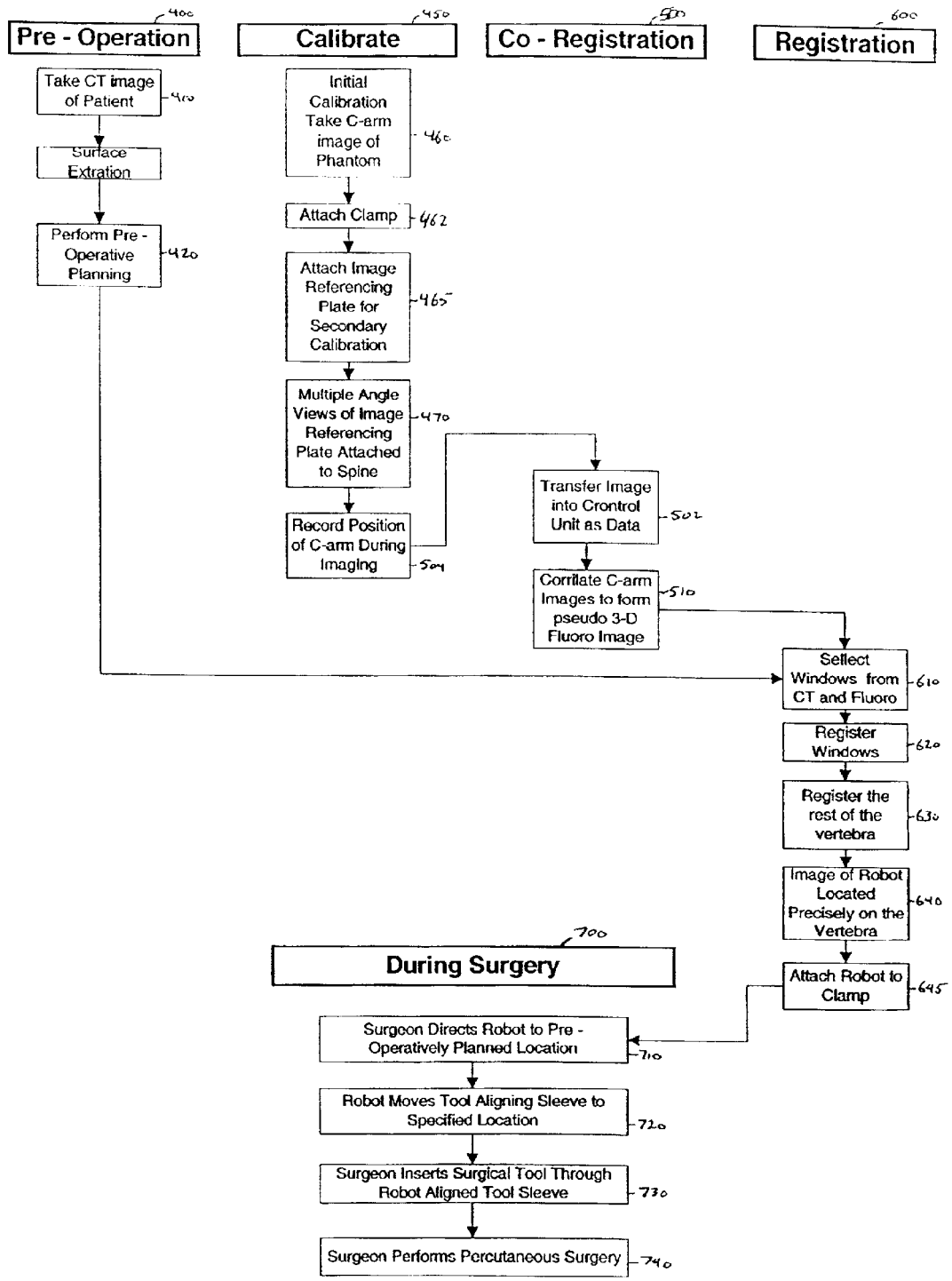
FIG. 5 is a flow chart of an embodiment of the method of using the present invention.

FIG. 5 illustrates the registration system used to establish the position of the robot on the bone. Initially there is a pre-operative step 400. This step 400 consists of taking a three-dimensional scan 410 of the patient, such as a CT or MRI scan. A surgeon then performs pre-operative planning 420 on the three-dimensional scan. For example, if the procedure to be done is a fracture fixation, the surgeon will study the three-dimensional image and the condition of the bone, choose the proper implant from a database containing implants of all types and sizes based on the present application, and electronically position and insert the implant, the screw, or the like. The parameters generated by the pre-operative planning 420 are stored in the control unit 10 for positioning the robot 30 during the actual surgical procedure.

In an exemplary embodiment, the three-dimensional imaging may be accomplished through manipulation of triangle vertices using linear interpolation of the acquired three dimensional data. An algorithm can be used to create triangle models of constant density surfaces from the three dimensional data while providing a high-resolution three dimensional surface construction so that the models have extensive detail and accuracy. There are four steps to accomplish this, the last three steps being resolvable by one algorithm. The four steps are: data acquisition, image processing, surface construction, and display.

The data acquisition is performed through standard medical imaging techniques which provide information from the patient either through computed tomography (CT), magnetic resonance (MR) or single photon emission computed tomography (SPECT). The next step, image processing is achieved by use of algorithms. The surface is then constructed through a three dimensional model, this surface is then displayed using realistic image that provides for shading and ray casting.

An algorithm known as the marching cubes algorithm may be used to assist in refining the surface so that it provides a more realistic picture for the surgeon. The surface construction is essentially a two step process of first locating the surface, which corresponds to a user-specified value, and then calculating norms at each vertex of each triangle. This algorithm utilizes cubes created from pixels to process local vertices and the intersections. First, the surface corresponding to a user specified value is located and triangles created, then the algorithm determines how the surface intersects the cube that was created from the pixels. This process is accomplished by assigning the vertices of each cube a value and comparing it to the value of the surface. The process results in 256 possible ways for the surface to intersect the cube. However, two symmetries of the cube, topology and rotational symmetry, are used to reduce the number of possibilities to fourteen. After the number of cases is reduced an index is created for each of the fourteen possible cases. This index allows for the identification of surface intersections and then linear interpolation can be utilized to develop the surface. A surface of constant density has a zero gradient component along the surface tangential direction, so the direction of the gradient vector is normal to the surface. From this knowledge, the surface normal vector can be determined assuming the magnitude of the gradient vector is nonzero. Because the surface of interest is between tissues of different densities, the gradient vector is nonzero. The gradient vector is the derivative of the density function.

Therefore to approximate the gradient vector, the gradient vector is estimated at the cube vertices and then linearly interpolated at the point of intersection. This estimation is accomplished using the differences of the densities at a given pixel and dividing that by the lengths of the cube edges. The calculation results in the unit normal which is then linearly interpolated to the point of intersection. The unit normal is calculated for each triangle vertex and the algorithm uses this unit normal to produce Gourad-shaded images. The marching cubes algorithm creates a surface from a three dimensional data set and has been applied to two dimension data from CT, MR, and SPECT scans to successfully give a resulting three dimensional view for medical applications. More details of the image reconstruction process are described for example in Lorensen et al., "Marching Cubes: a high resolution 3D surface reconstruction algorithm," Computer Graphics 21(1987) 163–169 which is incorporated herein by reference.

Figure 6:
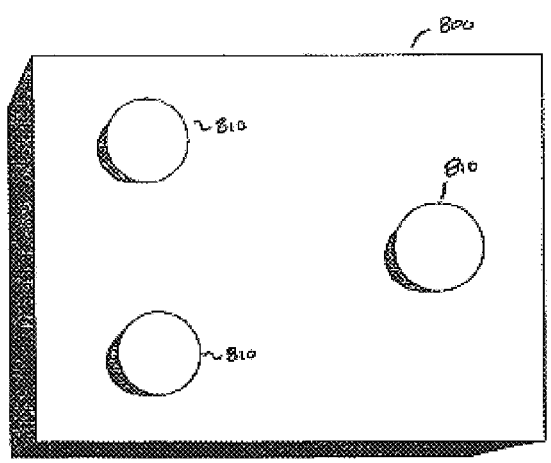
FIG. 6 is a perspective view of an image referencing plate with three referencing markers attached.

With reference now to FIGS. 1, 5, and 6 the next step is initial calibration of the C-arm 450. A phantom 320 (FIG. 1) is attached to the lens of the C-arm device 300 and a blank C-arm image is taken, step 460, FIG. 5. The phantom 320 is used to correct for the distortion associated with the C-arm image. The phantom contains several reference objects and a large number of small reference objects. The control unit automatically recognizes the reference objects and creates distortion correction maps and calibrates intrinsic parameters to correct for the imprecise C-arm image. Systems such as these for calibration are known in the art.

One such method for distortion correction utilizes a system which combines an x-ray camera connected to a control computer with an infrared tracking system linked to the control computer. In this method of distortion correction, the training of distortion parameters is combined with infrared tracking. The x-ray camera is calibrated, to correct for the distortion caused by the earth's magnetic fields, such distortion is dependent on the camera's position. Using the x-ray camera infrared tracking system, there are three steps for successful camera calibration to remove the distortions. The first step calibrates the x-ray camera by use of a fixed three dimensional coordinate system represented by a static calibration object and a second calibration object to determine the distortion properties. Distinct markers are used for each calibration object. The camera images are then smoothed and a set of connected regions in the image is obtained. Error minimization between the actual and the anticipated projections of the markers is accomplished by use of a cubic polynomial. This step, also referred to as coupled calibration, performs an error minimization between the anticipated and actual projections of the calibration markers, it utilizes a cubic distortion model to correct the resultant bending of the straight line into an S curve. Measurements are taken between the distorted actual image point and the projected point. Although this provides for some distortion correction, still, the camera parameters must be decoupled to correct for divergence, local minima, and the dependency of the coupled calibration on the initialization.

The second step, also known as decoupled parameters, need not be done intra-operatively as the infrared system is static, and the correction can be made based upon a fixed camera placement. The image is placed in the surface of calibration dish and the distortion parameters are determined. The correction polynomials applied are only partially cubic and are linearly dependent on the distortion parameters. The resulting function is quadratic and is solved analytically.

The final step eliminates the need for intra-operative calibration and marker detection. The actual camera placement and the corresponding distortion parameters from the earlier steps are utilized in what is referred to as the "learning mode." The "learning mode" constitutes taking pre-operative images and computing the corresponding distortion correction parameters by spline interpolation. The calibration is accomplished by using a pointer tracking system and matching the pre and intra-operative contours. This last step of the overall calibration method works however, only if the intra-operative viewing angles are limited to those in close vicinity to the pre-operative viewing angles. Further details of such a distortion correction system are described, for example, in Brack et al., "Accurate X-ray Navigation in Computer-Assisted Surgery", Proc. Of the $12^{th}$ Int. Symp. On Computer Assisted Radiology and Surgery, H. Lemke, et al., eds., Springer, 1998, which is incorporated herein by reference.

Another method of distortion correction can be implemented for use with fluoroscopic images according to a preferred embodiment of the invention. Fluoroscopic x-ray images are frequently used in the medical field, but are plagued by substantial distortions which must be corrected in order to effectively utilize these images. These distortions, which include small radial distortions and scaling deviations, are a result of both C-arm armamature deflection and orientation. Fluoroscopic images must be dewarped, which may be accomplished by computing a dewarped map from a reference image. The distortion can be modeled either across the entire image as a single function or by tessellating the image view of the field into triangles or quadrilaterals and then computing individual distortion functions, which are determined by using bilinear interpolation. Since the individual distortion functions are more adaptable, this local method is often preferred. To determine the distortion factors, the necessary parameters are the relative position and the orientation of the camera with respect to the imaging plane, the focal length, the image center location, and the image scaling and radial distortion coefficients. The relationship between these parameters is obtained by formulating the transformation from the world coordinate to the camera coordinates, transforming the three dimensional camera coordinates into two dimensional coordinates in an ideal image and then adding radial distortion, shifting and scale. The equations are solved for the relative position and orientation parameters by resolving a set of linear equations. Based on the solved parameters, the remaining parameters are derived. The least squares method is then used to incorporate additional points. Since the C-arm distortion is orientation dependent, the process must be completed for a variety of orientations, focusing on the extremes to ensure correction parameters cover the entire field. More details of the process are described, for example in Yaniv et al., "Fluoroscopic Image Processing for Computer-Aided Orthopaedic Surgery", Proc. $1^{st}$ Int. Conf. On Medical Computing and Computer-Assisted Intervention, Lecture Notes in Computer Science 1496, Elsevier, et al., eds., 1998, which is incorporated herein by reference.

Furthermore, images may be enhanced by improvement in control and alignment of the C-arm. This type of improvement can be accomplished by the creation of a local coordinate system. A local coordinate system may be attached to the surgical tool, the patient, and the C-arm. Then the coordinate system of the surgical tool is converted to the coordinate system of the two dimensional C-arm image coordinate system. The transformation between the surgical tool and the ultimate image is provided in real-time by the various position sensors. The basis for the transformation is a linear cone beam projection model. The conversion of the C-arm projection from three dimensional space to two dimensional image is obtained preoperatively during the C-arm calibration. The constant projection parameters of the C-arm are acquired using a calibration probe containing steel spheres which is equipped with LED sensors. From these sensors, the position of each sphere can be calculated and subsequently assigned a corresponding position in the two dimensional image. The resulting system of equations are solved using an error minimizing algorithm. To further minimize errors resulting from stress-dependent deformation of the C-arm frame, additional LEDs are mounted to track the actual camera position for updating at the time of image acquisition. To the extent there is additional distortion in the image intensifier-TV chain of the C-arm, resulting in stationary pin cushion distortion, and also a small variable amount of distortion caused by magnetic fields, a bilinear interpolation algorithm may be used for correction. Further details are described in Hofstetter et al., "Fluoroscopy Based Surgical Navigation—Concept and Clinical Applications", Proc. 11$^{th}$ Int. Symp. on Computer Assisted Radiology and Surgery, H. U. Lemke, et al., eds., Springer 1997, which is incorporated herein by reference.

A further method for three dimensional camera calibration utilizes a two step technique. Utilizing this two step approach, a real constraint or equation that is only a function of a subset of the calibration parameters is implemented. This reduces the dimensionality of the unknown parameter space.

The first step computes the three dimensional orientation and position. In this part of the process the distorted image coordinates are computed from the relationship between the distance between coordinate and the image center and an uncertainty scaling factor.

From these coordinates, the translation vectors and rotation factors are calculated. Using the translation vectors and rotation factors, the rotational matrix is determined.

The second step computes the effective focal length, distortion coefficients and third dimension position. These parameters are calculated from the relationship between the calibration points, the distances and the transformation matrix and rotation matrix from the first step.

This two step method is referred to as the "radial alignment constraint" and it is only a function of relative rotation and translation between the camera and the calibration points. The method is distinguishable from other methods in that the order of the transformation from the three dimensional camera coordinate to the image coordinate is rotation followed by translation as opposed to the reverse. Another benefit of this method is that it can be completed in real time. Furthermore, this method can also be used for calibrating a camera using monoview noncoplanar points and multiple viewing positions. Additional details are described in Tsai et al., "A Versatile Camera Calibration Technique for High-Accuracy 3D Machine Vision Metrology Using Off-the-Shelf TV Cameras and Lenses", IEEE Journal of Robotics and Automation, Vol. RA-3, No. 4, August 1987 which is incorporated herein by reference.

One of ordinary skill in the art will appreciate these aforementioned methods of calibration are exemplary and not limiting on the C-arm calibration method that may be employed by the present invention.

Next, the patient is brought into the operating room, a small incision is made according to standard surgical practice at the site where clamp 40 is to be attached, and the clamp is attached to the selected bone using handles as described above, step 462, FIG. 5. Handles 210 are then removed from the clamp 40. An image referencing plate 800 (FIG. 6) is attached to clamp 40, step 465, FIG. 5, by receiving holes that receive connector pins 200. The image referencing plate 800 (FIG. 6) has three referencing markers 810 on it that show up very clear and precise in the C-arm image. The distance and angle between the referencing markers 810 are known such that the C-arm image can be calibrated in a secondary calibration step, step 465, to accurately represent actual size of the image. At least two, but preferably three C-arm images are taken of the patient with the attached clamp 40 and image referencing plate 800. These C-arm images are taken from different angles, preferably 0, 45, and 90 degrees, step 470, FIG. 5.

In another embodiment of the present invention the secondary calibration step, step 465B, can be accomplished by attaching the robot 30 to the clamp and taking multiple C-arm images. By knowing the dimensions, or by placing referencing markers on robot 30 and knowing the distance and angle between the referencing markers the C-arm images can be calibrated in a secondary calibration step, step 465B.

The next step of the process is co-registration, step 500. The C-arm images are transferred into the control unit10 as data, step 502. At each location an image is taken from, the position of the C-arm is recorded, step 504, into the control unit 10. The data of the images, step 502, and the position of the C-arm, step 504, are correlated by knowing the position from which each images was taken, step 504, and by aligning the referencing markers 810 (FIG. 6) from the image referencing plate 800 (FIG. 6). Thus, an accurate, pseudo three-dimensional image of the surgical site with the clamp 40 attached to the bone is generated. This stage can be referred to as robot to bone registration or co-registration.

According to a preferred embodiment of the invention, bone to bone registration next occurs in step 600. Step 600 is a process of estimating and matching the true surface contours or the objects in the images. Registration methods are either based on geometry or intensity of the image. Geometric based registration is achieved by finding features in the two dimensional fluoroscopic images and matching these features with corresponding features in the three dimensional image, acquired, for example, from a CT scan dataset, MRI image, ultrasound image or from a CAD model. The features can be known landmarks (anatomical landmarks or implanted fiducials), or contour points in the fluoroscopic image, matched with the registered object's surface. An algorithm that may be used to compute the transformation is the Iterative Closest Point (ICP) algorithm. The ICP algorithm is an iterative alignment algorithm that works in three phases: first it establishes correspondence between pairs of features in the two structures that are to be aligned based on proximity, next it estimates the rigid transformation that best maps the first member of the pair onto the second and third, it applies that transformation to all features in the first structure. These three steps are then reapplied until convergence is concluded. The ICP algorithm relies on a convergence theorem. The key differentiation between the least squares registration and the ICP is the least squares generically reduces the average distance between corresponding points during each iteration whereas the closest point determination generally reduces the distance for each point individually. Further details on the use of the ICP algorithm are described in Besl et al., "A Method for Registration of 3D Shapes", IEEE Trans. on Pattern Analysis and Machine Intelligence, 1992, 14(2), 239–255, which is incorporated herein by reference. The input to the algorithm are sets of back-projected rays from the fluoroscopic images, and a model of the registered object. The algorithm iteratively computes a transformation that approximates the ray sets to the model. For landmark registration, a match between each ray and the corresponding landmark is defined before searching for the transformation. Contour registration selects a new surface point to match with each ray on every iteration.

Preferably, the registration process uses two or more fluoroscopic images. One method of automatic registration can be represented by a cooperative approach between registration and segmentation of pre-operative surface models and intra-operative x-ray images. The cooperative approach undertakes four steps: presegmentation, transformation, extraction, and error minimization. Presegmentation extracts contour points. These contour points correspond to pixels with large variations in grey-level intensity. The contour points are organized in chains of connected pixels with like grey level intensity resultings in automatic edge detection of an image. Then initial registration completes the segmentation to extract likely contours on x-ray images. This is done by identifying multiple pixels on anatomical landmarks and defining these pixels on x-ray images, thus ensuring the same landmarks are selected on the three dimensional surface model. These two sets of matched pixels are used cooperatively to estimate the initial transformation. The automatic edge detection results in an excessive number of contour points therefore it is necessary to eliminate pixels which do not correspond to contour points that are of interest. From the automatic edge detection weight must be given to each pixel in order to determine the likelihood that it is a real contour pixel; this determination is made by summing the gradient value, the size of the connected component and a distance factor. The first two components come from the x-ray image while the third depends upon information from the initial registration process. The distance calculation is performed utilizing an algorithm which minimizes energy and distance to account for internal and external contours, one such algorithm that may be used is the Levenberg-Marquardt algorithm. Further details of preferred registration procedures are described in Hamadeh, et al., "Towards automatic registration between CT and X-ray images: cooperation between 3D/2D registration and 2D edge detection, "Medical robotics and computer assisted surgery, 1995, Wiley 39–46 and Hamadeh, et al., "Automated 3-Dimensional Computed Tomographic and Fluoroscopic Image Registration", Computer Aided Surgery, 1998, 3. Both of these articles are incorporated herein by reference.

According to the registration method described above, anatomical landmarks in the images are detected and matched manually. Based on this match, an approximated initial guess is computed, with ray intersections, which are three dimensional points in the registration environment, being matched with the model's landmarks. Then, the object's contour in the two dimensional image is registered with the model's surface. A likelihood estimator is used to remove outliers, or pixels not in the contour, from the sample point set. A signed distance function is defined to overcome any internal contours problems. The overall in-vitro accuracy of this method can be better than 2 mm.

While most registration processes involve multiple images, in one alternative, a single fluoroscopic image may be used. The use of a single fluoroscopic image may still achieved an accuracy of about 3 mm. This single fluoroscopic image technique is based on a combinatorial search among matches of three points and three rays. The match with minimal average distance for the registration is then selected. These points and rays are used to determine two initial registrations. In such a technique, both points and lines may be used to represent data. In the single fluoroscopic model, the three points and the three rays are registered and from this, two three-point registrations, designated by triangles can be found. From the triangle's vertices, nonlinear functions can be established and then solved for the two unknowns by applying the Levenberg-Marquardt algorithm. From these points the line can be determined and the point-line correspondence can be solved. The lines are then fixed while the points are permuted resulting in three points in the back-projected lines. Horn's method is then used for the transformation into a frame and the ICP algorithm is implemented to determine the best match points for the registration. Further details of this technique are described in Tang, "Method for Intensity-based Registration with CT Images," Masters Thesis: Department of Computer Science, Queen University, Ontario Canada, 1999, which is incorporated herein by reference.

In a further alternative according to the invention, intensity-based registration is achieved by comparing fluoroscopic images with simulated X-rays (digitally reconstructed radiographs, or DRR's) from an estimated position. In this alternative, three types of coordinate systems are involved in the registration process: the CT coordinate system, the world coordinate system, and the radiographic coordinate system. The registration process consists of determining the CT to world transformation matrix, also known as the volume transformation matrix.

For each radiograph, the radiograph to world transformation matrix is derived. An iterative procedure is used to adjust the translation and orientation of the computed tomography (CT) data in the world coordinate system until a best match with the DRR is found. Next the radiographic to world transformation is accomplished. Translation, rotation, and scaling matrices are applied to the available data to complete and validate the registration. From these matrix calculations, the world coordinate of any voxel, three dimensional pixel, can be calculated.

To achieve the best match between the CT and the DRR, two elements are required, a cost function (the inverse of measure of similarity) and an algorithm for minimizing the cost function. Two costs functions are considered: the cross correlation of the pixel values and the magnitude of the scalar product of the gradient. The cross correlation is a function of the Pearson's product-movement coefficient and the number of nonvoid pixels. The gradient is a function of the product of the gradients in the plain radiographs and the DRR weighted by the number of pixels. The relative merit of the cost functions is analyzed in the vicinity of the stereotactic registration point. The stereotactic registration error and the extent of parameter space around the minimum devoid of local minima along the axis are the applicable criteria. A minimization algorithm based on patient orientation during the image acquisition and the assumption that the CT and radiographic acquisitions are such that the x-rays are nearly parallel to the CT slices is most effective in solving the registration problem.

The registration process as described in this alternative can be completed either semi-automatically or automatically. In semi-automatic registration, a mouse driven interface can be used to initiate the registration process and provide for the rotation and translation of the CT parameters. Automatic registration can be accomplished by utilization of biscalar algorithms for translation, complimented by Powell's algorithm for exploration of the full six-dimensional rotation parameter. The method of automatic registration comprises eleven steps: an eight-step orientation algorithm followed by the three-step six-dimensional minimization algorithm. Further details are described in Lemieux et al., "Patient-to computed-tomography image registration method based digitally reconstructed radiographs", Medical Physics, 21, 1994, 1749–1760 which is incorporated herein by reference.

Another type of registration that may be implemented in the invention is intensity based registration. Intensity based registration is utilized to develop an improved automatic beam alignment process for frameless image-guided radiosurgery. Utilizing this mode of registration, radiographs acquired during patient treatment can be coordinated with DRRs generated from a CT study representative of hypothetical patient positions which involve three translations and three rotations. This method of registration has three parts: developing a means of exploring the range of possible patient positions; identifying those elements of images that effectively capture the patient pose; and using a comparison statistic or cost function for the two sets of image feature data to indicate when the best match has been accomplished. There are three ways to analyze DRRs and complete the match for this method of registration: the matched filter area correlation; the interpolative area correlation; and the iterative reprojection. The preferred method is the iterative reprojection because it is executed in real time. Along with the necessary correlation corrections, the comparison between the DRRs and the radiographs poses the problem of pattern recognition which must also be resolved during registration. The image data used is referred to as feature vectors; these vectors may be primitive or highly sophisticated. The registration algorithm provides for an independent check on the edge detection process as well as the region of interest. The registration algorithm employs six free parameters to minimize the chi-statistic which is consists of the weighted vector components. The minimization problem is nonlinear and solved with a hybrid algorithm that starts with a gradient search and progresses to a Taylor series approximation. Using the iterative reprojection method, an algorithm may be designed such that the registration process is completely automated, reliable, and speedy, however, it is necessary to identify the areas of interest prior to registration. Further details on such techniques are described for example, in Murphy, M. "An automatic six-degree-of freedom image registration algorithm for image-guided frameless stereotactic surgery", Medical Physics, 24(6), June 1997 which is incorporated herein by reference.

When the camera position guess and the actual position are very close, the original and reconstructed image are very similar. Pixel intensity information is used to define a measure of similarity between the datasets. The similarity measure can include intensity values, cross-correlation, histogram correlation, and mutual information. The algorithm proceeds in three steps. The input is a CT data set, intrinsic camera parameters, one or more fluoroscopic images and an initial camera position estimate for each image. In the first step, the algorithm generates one DRR for each given camera position. In the second step, a dissimilarity measure is computed between the real and reconstructed image. In the third step, new camera poses are computed that best reduce the dissimilarity between the images. The process is repeated until convergence is reached. The parametric space of camera positions in then searched incrementally from an initial configuration. The space is six-dimensional (three rotations and three translations). The advantages of this technique is that no segmentation is necessary. However, the search space is six-dimensional, and can contain may local minima.

A benefit of the present invention is that it can utilize either of the above described registration methods. By utilizing the dimensions of the bone attached robot and its attachment location, the initial location of the window is a very good guess of the location and therefore the intensity based method can be utilized. Thus, according to the present invention, a faster and more accurate registration process is accomplished as between the fluoroscopic and three dimensional images. This is done in step 600, and occurs very quickly and with a high degree of accuracy because the registration process is performed on small windows of the images, rather than the images as a whole. Preferably windows are selected that specifically relate to the known location of the robot and/or its support member. Windows of about 20 mm by 20 mm located approximately adjacent to the clamp location, according to pre-operative calculation of the bone-robot attachment location, are selected from the C-arm (fluoroscopic) image data, step 610. For example, these windows may be selected as the area above the attached clamp 40 in the C-arm image and the tip of the transverse process of the vertebra covering the area where the surgical procedure is to take place. Generally, the same windows are chosen from both the pseudo three-dimensional hybrid C-arm image, step 510, and also from the CT image (three dimensional image), step 410. The small windows chosen from the C-arm images and the CT scan image are then laid over each other and matched or registered by the control unit, step 620, as described above. Focusing only on a small window of the C-arm image rather than looking for a matching anatomical landmark in the entire image, makes the process occur very fast and with the high degree of accuracy needed for precise procedures such as vertebra surgery.

Next, the remaining portion of the CT and C-arm image of the bones are overlaid, the registration windows are aligned, and the remaining bone is registered, step 630. Since the windows have already been accurately registered this step occurs quickly and also with a high degree of accuracy. Now clamp 40 is located precisely on the bone, step 640, of the CT image. Next, the user attaches robot 30 to clamp 40 and thus, robot 30 is located precisely with respect to the bone, step 645.

After robot 30 is co-registered 500 and registered 600, its position is known relative to the patient's bone and therefore can move to align with the pre-operatively picked location such that the operation can virtually take place on the control unit. The user selects a pre-operatively planned location and task from step 420 by use of a joystick, mouse, touch screen, or the like, step 710. The robot 30 responds and moves sleeve 60 into position, step 720, such that when the user inserts a surgical tool 70 through the opening in the sleeve 60 the surgical tool 70 will be precisely aligned with the location requiring the surgical procedure, step 730. The surgeon can then insert a selected surgical tool 70 and operate without opening the surgical site to see the placement of the surgical tool because the surgeon can verify the positioning of the surgical tool 70 on the control unit 10 and display 20. Thus operating percutaneously or in general open procedures, with a high degree of accuracy, low trauma, small incisions, low chance of infection, and minimal exposure to radiation. A further benefit of this system is that because the robot is miniature it can be freely attached to the bone of a patient and move with the body. Therefore, the robot system does not need a dynamic referencing device to maintain orientation with the body once it is registered. This creates a more precise and less complicated system that is versatile and user friendly as the surgeon can manipulate the patient into different surgical positions without disturbing the robot system.

The present invention is illustrated herein by reference to a spinal vertebra attachment. However, it will be appreciated by those in the art that the teachings of the present invention are equally applicable to other bone attachments.

What is claimed is:

1. A surgical system, comprising:
   a surgical robot for manipulating a surgical tool to a surgical site during a surgical procedure;
   an attachment member configured and dimensioned to mount the surgical robot on a bone associated with said surgical site, such that said robot is supported in its entirety by said bone; and
   a controller programmed prior to said surgical procedure to direct the robot to position the surgical tool at the surgical site.

2. The surgical system according to claim 1, wherein said robot comprises:
   a base member;
   at least four actuators extending outward from the base member at fixed angles, said actuators being arranged in cooperating pairs, said pairs together defining a spherical joint at cooperating ends opposite the base member, and
   a surgical tool held by said spherical joints.

3. The surgical system according to claim 2, wherein said actuators define a longitudinal axis and are configured to provide only translational movement along said axis.

4. The surgical system according to claim 2, wherein surgical site lies at least approximately within a defined plane and said surgical robot is configured and dimensioned such that said base member is at least approximately perpendicular to said defined plane.

5. The surgical system according to claim 1, wherein said surgical tool comprises at least one of a tool guide, a cutting member and a drilling member.

6. The surgical system according to claim 1, wherein said robot comprises a miniature parallel robot.

7. The surgical system according to claim 1, wherein said attachment member comprises a robot receiving adaptor mounted on a bone attachment portion.

8. The surgical system according to claim 7, wherein said bone attachment portion comprises a clamp having at least two jaws shaped to mate with a specific bone configuration.

9. The surgical system according to claim 7, wherein said bone attachment portion comprises at least one wire configured and dimensioned to be received in bone holes.

10. The surgical system according to claim 1, wherein said controller comprises a cpu and user interface communicating with said robot, said cpu containing a program for guiding the robot based on data generated from surgical site images.

11. The surgical system according to claim 10, wherein said surgical site images are created prior to each surgical procedure requiring a new location for the support member.

12. The surgical system of claim 1, wherein said controller is further programmed to locate said surgical robot with respect to a patient anatomy based on at least one of at least one three dimensional pre-operative patient image and at least one further intra-operative patient image including said attachment member.

13. The surgical system of claim 12, wherein said controller is further programmed with instructions for execution of a surgical plan based on said determined surgical robot location.

14. The surgical system of claim 1, wherein said controller is further programmed with instructions for registering said surgical robot positionally with at least one pre operative three dimensional image of a patient.

15. A surgical system of claim 1, wherein said robot comprises at least 3 actuators mounted on said base member, at least one of said actuator being configured for at least translational or rotational movement.

16. A surgical system for facilitating a surgical procedure at a surgical site, comprising:
    a surgical robot comprising a base member; two pairs of actuators extending outward from the base member at fixed angles, wherein said actuators each have first and second ends, said first ends of a pair being spaced apart on said base member and said second ends of a pair coming together to define a tool holding element;
    an attachment member removably securable to the robot base member and configured and dimensioned to mount the surgical robot on a bone associated with said surgical site, such that said robot is supported in its entirety by said bone; and
    a controller including a cpu and user interface communicating with said robot, said cpu containing a program for guiding the robot based on data generated from surgical site images created prior to said surgical procedure.

17. A surgical system, comprising:
    a surgical robot for manipulating a surgical tool to a surgical site during a surgical procedure;
    an attachment member comprising a bone attachment portion configured for mounting on a patient bone, such that said robot is supported in its entirety by said bone; and
    a robot receiving portion mounted on said bone attachment portions,
    wherein said robot receiving portion is alignable on said bone attachment portion to provide a robot receiving surface of a selected orientation; and
    a controller programmed to locate said surgical robot with respect to a patient anatomy.

18. The surgical system of claim 17, wherein a selected orientation of said robot receiving surface is horizontal.

19. The surgical system of claim 17, wherein said controller is further programmed with instructions for execution of a surgical plan based on said determined surgical robot location.

20. The surgical system of claim 17, wherein said controller is further programmed with instructions for registering said surgical robot positionally with at least one pre operative three dimensional image of a patient.

21. The surgical system of claim 17, and also comprising a clamp adapter attached to said bone attachment portion, wherein said bone attachment portion includes at least one substantially spherical mating surface for mating with the robot receiving portion, and wherein said substantially spherical mating surface provides a selectable range of orientation for said clamp adapter.

22. The surgical system of claim 17, wherein said bone attachment portion of said attachment member includes first and second opposing clamp jaws configured to clamp onto a bone of a patient.

23. The surgical system of claim 22, wherein said bone attachment portion further comprises first and second locking assemblies.

24. The surgical system of claim 23, wherein said first locking assembly comprises:
   a first lever pivotally mounted on the first jaw;
   a second lever pivotally mounted on the second jaw; and
   a pivot interconnecting said first lever and said second lever.

25. The surgical system of claim 23, wherein said second locking assembly comprises:
   a first threaded stud coupled with said first lever and extending to receive said robot receiving portion;
   a second threaded stud coupled with said second lever and extending to receive said robot receiving portion; and
   nuts received on said first and second threaded studs for coupling said bone attachment portion with said robot receiving portion.

26. A surgical system for performing a procedure at a surgical site wherein a bone is associated with the surgical site and has a known relationship to the surgical site, said system comprising:
   a surgical robot for manipulating a surgical tool at the surgical site;
   an attachment member configured and dimensioned to be attached directly to the bone to define a fixed orientation between the bone and surgical robot; and
   a controlled programmed prior to the surgical procedure to direct the robot to position the surgical tool with respect to the surgical site based at least in part on said fixed orientation.

27. The surgical system of claim 26, wherein said attachment member is configured and dimensioned to cooperate between the bone and the robot to correspondingly reorient the robot in response to a reorientation of the bone resulting from movement of the bone whereby said fixed orientation is maintained.

28. The surgical system of claim 27, wherein said attachment member comprises a bone attachment portion and a robot receiving portion, the bone attachment portion being configured for attachment to the bone and the robot receiving portion being mountable on the bone attachment portion for receiving the robot such that said fixed orientation is selectable.

29. A surgical system, comprising:
   a surgical robot for manipulating a surgical tool to a surgical site during a surgical procedure;
   an attachment member configured and dimensioned to be attached directly to a bone associated with the surgical site, said attachment member providing a fixed orientation between the bone and surgical robot such that a reorientation of the bone resulting from movement of the bone results in a corresponding reorientation of the robot whereby said fixed orientation is maintained; and
   a controller programmed prior to the surgical procedure to direct the robot to position the surgical tool with respect to the surgical site based in part on said fixed orientation.

* * * * *